US006440930B1

(12) United States Patent
Rinella, Jr.

(10) Patent No.: US 6,440,930 B1
(45) Date of Patent: Aug. 27, 2002

(54) PROTEIN FORMULATIONS

(75) Inventor: Vincent Joseph Rinella, Jr., Brownsburg, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/787,500

(22) PCT Filed: Sep. 14, 1999

(86) PCT No.: PCT/US99/21055

§ 371 (c)(1),
(2), (4) Date: Mar. 16, 2001

(87) PCT Pub. No.: WO00/15224

PCT Pub. Date: Mar. 23, 2000

Related U.S. Application Data

(60) Provisional application No. 60/100,687, filed on Sep. 17, 1998.

(51) Int. Cl.[7] .......................... A61K 38/00; A61K 31/44
(52) U.S. Cl. ............................ 514/2; 514/356
(58) Field of Search ...................... 514/2, 356

(56) References Cited

U.S. PATENT DOCUMENTS

| | | | | |
|---|---|---|---|---|
| 4,816,401 A | * | 3/1989 | Taupier et al. | 435/240.31 |
| 5,118,666 A | | 6/1992 | Habener | 514/12 |
| 5,120,712 A | | 6/1992 | Habener | 514/12 |
| 5,382,574 A | | 1/1995 | Jorgensen | 514/3 |
| 5,405,945 A | | 4/1995 | Boime et al. | 536/23.51 |
| 5,512,549 A | | 4/1996 | Chen et al. | 514/12 |
| 5,545,618 A | | 8/1996 | Buckley et al. | 514/12 |
| 5,639,640 A | | 6/1997 | Reddy et al. | 435/325 |
| 5,686,113 A | * | 11/1997 | Speaker et al. | 424/490 |
| 5,705,483 A | | 1/1998 | Galloway et al. | 514/12 |

FOREIGN PATENT DOCUMENTS

| | | |
|---|---|---|
| WO | WO 91/11457 | 8/1991 |
| WO | WO 98/08871 | 3/1998 |

OTHER PUBLICATIONS

Fawzi, et al., *J. Pharmaceut. Sci.* 69:104–106 (1980).
Truelove, et al., *Int. J. Pharmaceutics* 19:17–25 (1984).
Hamza, et al., *Drug Dev. Industr. Pharmacy* 11 (8) : 1577–1596 (1985).
Rasool, et al., *J. Pharmaceut. Sci.* 80:387–393 (1991).
Hussain, et al., *J. Pharmaceut. Sci.* 82:77–79 (1993).
Coffman, et al., *J. Pharmaceut. Sci.* 85 (9) :951–954 (1996).
Shome B., et al., *J. Protein Chem.* 7 (4) :325–339 (1988).
Saxena B. B. and Rathnam P., *J. Biol. Chem.* 251 (4):993–1005 (1976).
Watkins, et al., *DNA* 6(3) :205–212 (1987).
Shome B. and Parlow A.F., *J. Clin. Endocrinol. Metab.* 39 (1) :203–205 (1974).
Beck, et al., *DNA* 4:76 (1985).
Amoss, et al., *J. Clin. Endocrin. Metab.* 39:187–190 (1974).
Sairam, et al., *Biochem. J.* 197:541–552 (1981).
Closset, *Eur. J. Biochem.* 86:115–120 (1978).
Fujiki, *J. Biol. Chem.* 253 (15) :5363–5368 (1978).
Mentlein, R., et al., *Eur. J. Biochem.* 214:829–835 (1993).

* cited by examiner

*Primary Examiner*—Raymond Henley, III
(74) *Attorney, Agent, or Firm*—Mark J. Stewart; Paula K. Davis

(57) ABSTRACT

The present invention discloses a stable, soluble formulation comprising a medically useful peptide or protein, a hydrophobic preservative, and nicotinamide. Said storage-stable, soluble formulation is useful as a multi-use pharmaceutical product.

21 Claims, 1 Drawing Sheet

PROTEIN FORMULATIONS

This is a 371 of PCT/US99/21055 filed Sep. 14, 1998 which claims the benefit of U.S. Provisional Application No. 60/100,687 filed Sep. 17, 1998.

FIELD OF INVENTION

The present invention is in the field of peptide and protein chemistry as it applies to human medicine. In particular, the invention relates to the preparation of soluble stabile peptide and protein formulations that include nicotinamide and hydrophobic preservatives.

BACKGROUND OF THE INVENTION

Nicotinamide is not a widely-recognized excipient in pharmaceutical formulations. For example, it is not mentioned as an excipient in the *Handbook of Pharmaceutical Excipients*, 2nd ed., A. Wade & P. Weller, Eds. (1994). However, nicotinamide is known to increase the solubility of sparingly-soluble, non-protein, low molecular weight compounds, such as, certain piperazido and piperazino compounds [Fawzi, et al., *J. Pharmaceut. Sci.* 69:104–106 (1980)], anti-cancer nucleoside analogs [Truelove, et al., *Int. J. Pharmaceutics* 19:17–25 (1984)], paracetamol [Hamza, et al., *Drug Dev. Industr. Pharmacy* 11:1577–1596 (1985)], diazepam, griseofulvin, progesterone, 17β-estradiol, and testosterone [Rasool, et al., J. Pharmaceut. Sci. 80:387–393 (1991)], the phenothiazine derivative, moricizine [Hussain, et al., *J. Pharmaceut. Sci.* 82:77–79 (1993)], and riboflavin [Coffman, et al., *J. Pharmaceut. Sci.* 85:951–954 (1996)].

In the above cited formulations, nicotinamide apparently operates as a hydrotropic agent to increase the solubility of another solute when nicotinamide is added at a high concentration. This hydrotropic phenomenon is in direct opposition to normal solution behavior where addition of a second solute to a solution of a sparingly soluble substance will cause the less soluble substance to precipitate.

A combination of insulin and nicotinamide, optionally containing a preservative, was previously described by Jorgensen in U.S. Pat. No. 5,382,574. The formulation was reported to promote faster absorption of insulin from an injection site. Jorgensen does not discuss any effect of nicotinamide on formulation stability. Moreover, it is likely that the effect of nicotinamide was not observerd or appreciated because the specification specifically recommends that known stabilizing agents such as phospholipids be added to stabilize the formulations. Also, it fails to mention any effect on insulin stability produced by nicotinamide alone.

The molecular interactions in peptide and protein formulations are complex because a variety of factors such as choice of preservative, buffer, ionic strength, pH, temperature, and other excipients must be balanced to produce a relatively stable formulation suitable for manufacturing, shipping, and storage that meets regulatory requirement for such products. The role that each factor contributes to aggregation is uncertain in view of the complexity of the given peptide or protein molecule as well as the propensity for that peptide or protein to aggregate and precipitate in formulations containing preservatives. In view of this complexity and tendency to aggregate, the effect of nicotinamide on the stability of peptides and protein formulations containing a hydrophobic preservative could not have been predicted from the art describing nicotinamide's effect as a hydrotropic agent for relatively small molecules, nor from its apparent ability to facilitate absorption of insulin from a subcutaneous injection.

Thus, the present invention provides conditions that increase the physical stability of medically useful peptides and proteins in the presence of hydrophobic preservatives and makes possible commercially-viable, multi-use soluble pharmaceutical products to treat a variety of human diseases.

SUMMARY OF THE INVENTION

This invention provides a stable soluble formulation comprising a medically useful peptide or protein, a hydrophobic preservative, and nicotinamide.

The invention further provides a process for preparing said formulation which comprises combining a peptide or protein, a hydrophobic preservative, and nicotinamide to produce said formulation.

DETAILED DESCRIPTION AND PREFERRED EMBODIMENTS

Figure 1:
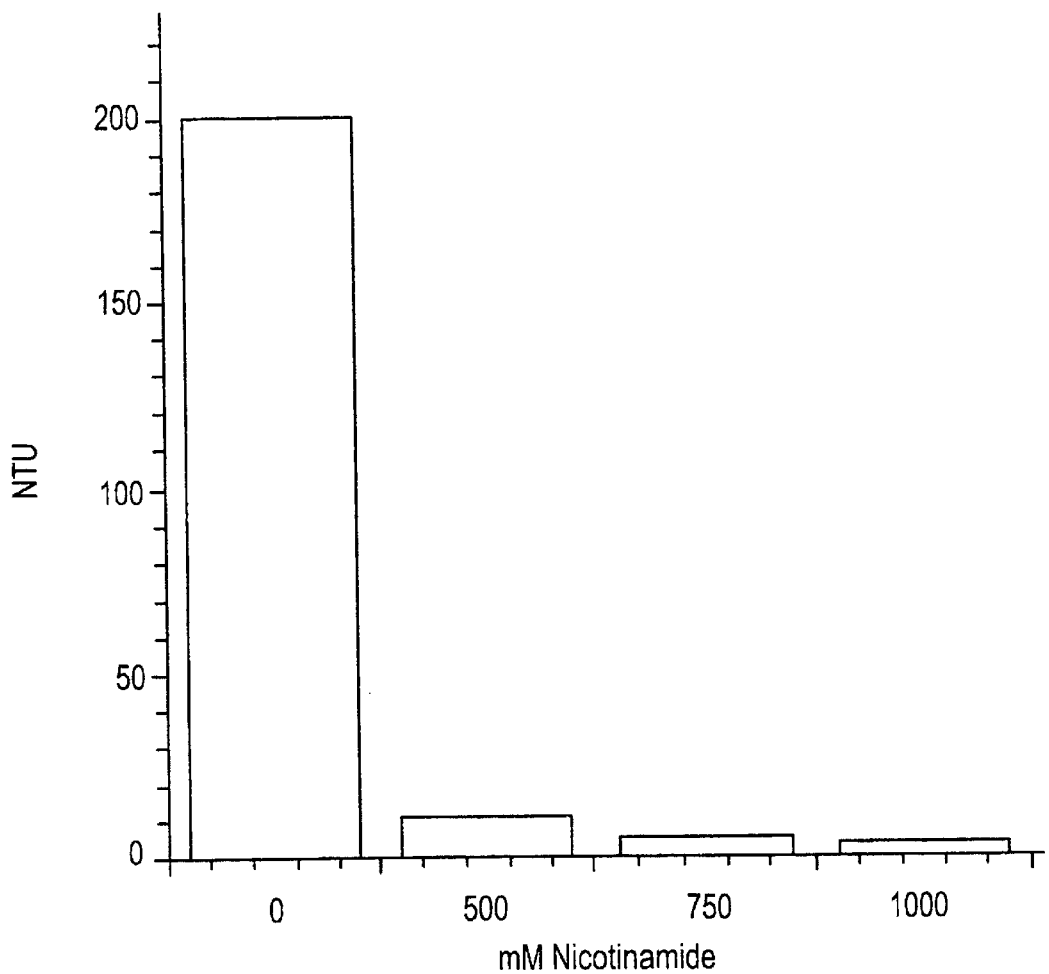
FIG. 1. Graph illustrating the turbidity (measured in NTU) of a solution containing 10 mg/mL hGH, 0.3% m-cresol, pH 6.0, 10 mM citrate, and nicotinamide of varying concentrations.

For purposes of the present invention, as disclosed and claimed herein, the following terms and abbreviations are defined as follows:

Administering—an act whose effect is to transfer a formulation of the present invention into the body of a mammal in need thereof. Administration may be via any route known to be effective by the physician of ordinary skill. Parenteral administration is commonly understood in the medical literature as the injection of a dosage form into the body by a sterile syringe or some other mechanical device such as an infusion pump. Peripheral parenteral routes of administration include, without limitation, intravenous, intramuscular, subcutaneous, and intraperitoneal routes of administration.

Alkylparaben—refers to a $C_1$ to $C_4$ alkyl paraben, or mixtures thereof. Preferably, alkylparaben is methylparaben, ethylparaben, propylparaben, or butylparaben.

Cresol—refers to meta-cresol, ortho-cresol, para-cresol, chloro-cresol, or mixtures thereof.

Hydrophobic preservative—refers to a hydrophobic compound that is added to a pharmaceutical formulation to act as an anti-microbial agent. A parenteral formulation must meet guidelines for preservative effectiveness to be a commercially viable multi-use product. Among hydrophobic preservatives known in the art as being effective and acceptable in parenteral formulations are the alkylparabens, the phenolic preservatives, benzyl alcohol, chlorobutanol, benzoic acid and various mixtures thereof. See, e.g., WALLHAUSER, K.-H., DEVLOP. BIOL. STANDARD. 24, pp. 9–28 (Basel, S. Krager, 1974).

Isotonicity agent—refers to a compound that is tolerated physiologically and imparts a suitable tonicity to the formulation to prevent the net flow of water across cell membranes. Compounds, such as glycerin, are commonly used for such purposes at known concentrations. Other possible isotonicity agents include salts, e.g., NaCl, and sugars, e.g., dextrose, mannitol, and sucrose.

Nicotinamide—refers to a compound of the formula:

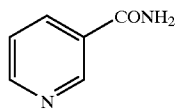

Pharmaceutically acceptable buffer—The pH of the formulation may be buffered with a pharmaceutically acceptable buffer, such as, without limitation, sodium acetate, sodium phosphate, sodium citrate, sodium tartarate, TRIS or a basic amino acid, such as, histidine, lysine or arginine. Other pharmaceutically acceptable buffers are known in the art. The selection and concentration of buffer is known in the art.

Phenolic preservative—refers to phenol and cresol.

Soluble—refers to the relative absence of aggregated protein that is visually perceivable. The degree of aggregation of proteins in a formulation may be inferred by measuring the turbidity of the formulation. The greater the turbidity of the formulation, the greater the extent of aggregation of the protein in the formulation. Turbidity is commonly determined by nephelometry, and measured in Nephalometric Turbidity Units (NTU).

Stable—A "stable" formulation is one in which the protein or peptide remains soluble for an extended period of time under the conditions of storage.

Treating—as used herein, describes the management and care of a patient for the purpose of combating a disease, condition, or disorder and includes the administration of a formulation of the present invention to prevent the onset of the symptoms or complications, alleviating the symptoms or complications, or eliminating the disease, condition, or disorder. Treating, as used herein, includes the administration of the protein for cosmetic purposes. A cosmetic purpose seeks to control the weight of a mammal to improve bodily appearance.

In one embodiment, the invention relates to formulations containing a hydrophobic preservative, nicotinamide and a medically useful peptide or protein. which are defined to include native hormones and functional analogs (excluding insulin and insulin analogs and leptin and leptin analogs), native cytokines and functional analogs, soluble protein vaccines, and antibodies and antibody fragments of all forms.

The following list of medically useful peptides and proteins is provided for illustrative purposes and is in no way meant to limit the scope of the medically useful peptides and proteins that are consistent with the invention: ocytocin, vasopressin, adrenocorticotropin hormone and analogs, epidermal growth factor, platelet-derived growth factor, prolactin, luteinising hormone releasing hormone, growth hormone, growth hormone releasing hormone, somatostatin, glucagon, GLP-1 related compounds, IL-2, IL-10, IL-15, interferon-α,β,γ, gastrin tetragastrin, pentagastrin, urogastrin, secretin, calcitonin, enkaphalins, endorphins, angiotensins, thyrotropin releasing hormone, tumor necrosis factor, nerve growth factor, granulocyte colony stimulating factor, granulocyte macrophage colony stimulating factor, macrophage colony stimulating factor, renin, bradykinin, bacitracins, polymixins, colistins, tyrocidin, gramicidins.

A more preferred group of medically useful peptides and proteins, defined as "Group I polypeptide" for purposes of this specification, consists of acylated insulins, particularly $C_6$–$C_{20}$ acylations of the epsilon amino group of Lys on the insulin B-chain, especially C14 acylated $Lys^{B28}$ $Pro^{B29}$ human insulin, mammalian growth hormone, growth hormone releasing hormone, GLP-1 related compounds, erythrocyte progenitor hormone (EPO), parathyroid hormone and fragments, especially as disclosed in U.S. Pat Nos. 4,086,196 and 5,208,041, β-lipotropin, fibroblast growth factor-8 and analogs, osteoprotegrin-2 and 3, interleukin-10 and 15 and their analogs, vascular endothelial growth factor, and follicle stimulating hormone (FSH) and variants.

Follicle stimulating hormone "FSH", whether produced recombinantly or isolated, and follicle stimulating hormone variants "FSH variants" as defined herein are well-known in the art. FSH as used herein refers to the FSH produced as a full length mature protein which includes, but are not limited to human FSH or "hFSH", whether produced recombinantly or isolated from human sources (see Shome B., et al.,*J. Prot. Chem.*, 7:325–339, 1988; Saxena B. B. and Rathnam P., J. Biol. Chem., 251:993–1005, 1976; Watkins, et al., DNA, 6:205–212, 1987; Shome B. and Parlow A. F., *J. Clin. Endocrinol. Metab.*, 39(1):203–205, 1974; and Beck, et al., DNA, 4:76, 1985; U.S. Pat. No. 5,405,945, and U.S. Pat. No. 5,639,640)each citation incorporated by reference. Furthermore, various FSH variants are known or are understood from the art (see Shome, J. Clin. Endocrin. Metab 39:187 (1974); Saxena, J. Biol Chem 251(4):993–1005 (1976); 1978; Sairam et al., Biochem J 197:541 (1981); additionally see Closset Eur. J. Biochem. 86:115–120; Fujiki, J. Biol. Chem. 253:5363–5368 (1978); Sairam, Biochem. J. 197:541–552 (1981)—each citation independently incorporated by reference). Prior-art FSH beta subunits would include the Saxena sequence as well as a genus of sequences implicated in Sairam's discussion of (a) evolutionarily conserved amino acids and (b) well-known and characterized errors in sequencing. Further, those of skill in the art recognize that the substitution of a prior art identified amino acid with (i) a chemically similar amino acid or (ii) an evolutionarily conserved amino acid would have no appreciable affect on the biological activity of an FSH heterodimer comprised of an hFSH beta subunit, thus modified.

In particular, Sairam's commentary on the Saxena hFSH sequence, as well as his discussion of amino acid substitutions identified between functional FSH molecules, defines a genus of FSH beta chain sequences in the prior art. More specifically, the 1981 Sairam publication identifies conserved amino acid sequences referring to publications by Saxena et al., Shome et al., Closset et al., and Fujiki et al. Sairam, Biochem J 197:541, 551 (1981). The prior art (1) evidences a preference for the FSH beta-chain sequence of Saxena over that of Shome; (2) addresses the issue of carboxy-terminal heterogeneity; (3) states that portions of the molecule affected by interspecies differences that are not essential for activity of the hormone and (4) highlights the guidance drawn from homologies between species and between the beta chains of the three, human glycoprotein hormones, FSH, LH and TSH.

C-terminal heterogeneity is reported for all the published sequences except for that of the porcine FSH-s, in which glutamic acid was the only C-terminal residue. For position 27, Saxena assigned one tryptophan residue to this position also found support in the evolutionary conservation demonstrated for a tryptophan at position 24 for FSH-B, among all prior art species. For positions 44 and 46, Saxena shows that, at position 44, the residue should be arginine instead of lysine and, at position 46, lysine instead of arginine. The porcine, equine and ovine sequences also reflected an evolutionary pressure to conserve the arginine at the position 44.

The variations at three positions, 21, 22 and 44 involve a structurally conservative or evolutionarily-conserved ("homologous") substitutions, each of which possess bioactivity.

Each of the Sairam, Shome, and Closset references disclose residues isoleucine, serine at positions 21–22, while Saxena discloses leucine, threonine and Fujiki discloses isoleucine, threonine at these positions. Each of these disclosures is not only an evolutionarily conservative substitution, but also a structurally conservative substitution. The variation at position 41 between the aspartic acid disclosed by each of Sairam, Shome, Closset, and Fujiki and the asparagine disclosed by Saxena, Closset and Sairam involves two evolutionarily conserved residues, each of which provide bio-activity. These disclosures of conservative substitutions and evolutionarily conserved substitutions guide the skilled artisan to distinct FSH beta chain variants, within the hFSH-B chain genus.

A more preferred group of medically useful peptides and proteins consists of GLP-1 related compounds and native mammalian growth hormone.

A more highly preferred group of peptides consistent with the present invention is glucagon-like peptide-1, its analogs and derivatives as defined herein.

Water soluble copolymers and polymer conjugates of the aforementioned peptides and proteins are also consistent with the present invention and include for example polyethylene glycol, copolymers of ethylene glycol/propylene glycol, carboxymethylcellulose, dextran, polyvinyl alcohol, polyvinyl pyrolidone, poly-1,3-dioxane, poly-1,3,6-trioxane, ethylene/maleic anhydride copolymer, polyaminoacids (either homopolymers or random or nonrandom copolymers copolymers), and dextran or poly(n-vinyl pyrolidone)polyethylene glycol, propylene glycol homopolymers polypropylene oxide/ethylene oxide co-polymers, polyoxyethylated polyols, polystyrenemaleate and polyvinyl alcohol. Polyethylene glycol propionaldenhyde is preferred.

The term "GLP-1" refers to human glucagon-like peptide-1 whose sequences and structures are known in the art. See U.S. Pat. No. 5,120,712, herein incorporated by reference. There are two native forms of human GLP-1, GLP-1(7-37)OH and GLP-1(7-36)NH$_2$ which will be distinguished only when necessary.

The term "GLP-1 analog" is defined as a molecule having one or more amino acid substitutions, deletions, inversions, or additions compared with GLP-1. Many GLP-1 analogs are known in the art and include, for example, GLP1(7-34) and GLP-1(7-35), GLP-1(7-36), Val$^8$-GLP-1(7-37), Gln$^9$-GLP1(7-37), D-Gln$^9$-GLP-1(7-37), Thr$^{16}$-Lys$^{18}$-GLP-1(7-37), and Lys$^{18}$-GLP-1(7-37). Preferred GLP-1 analogs are GLP-1(7-34) and GLP-1(7-35), which are disclosed in U.S. Pat. No. 5,118,666, herein incorporated by reference.

The term "GLP-1 derivative" is defined as a molecule having the amino acid sequence of GLP-1 or a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine e-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is $C_1$–$C_4$ alkyl. Furthermore, one or more side groups, or terminal groups, may be protected by protective groups known to the ordinarily-skilled protein chemist. The α-carbon of an amino acid may be mono- or di-methylated.

The term "GLP-1 molecule" means GLP-1, GLP-1 analog, or GLP-1 derivative.

Another preferred group of GLP-1 analogs is defined by the formula:

R$_1$-X-Glu-Gly-Thr-Phe-Thr-Ser-Asp-Val-Ser-Ser-Tyr-Leu-Y-Gly-
Gln-Ala-Ala-Lys-Z-Phe-Ile-Ala-Trp-Leu-Val-Lys-
Gly-Arg-R$_2$ 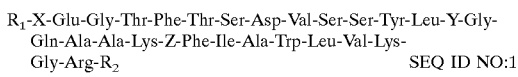

and the pharmaceutically-acceptable salts thereof, wherein: R$_1$ is selected from the group consisting of L-histidine, D-histidine, desamino-histidine, 2-amino-histidine, b-hydroxy-histidine, homohistidine, alpha-fluoromethyl-histidine, and alpha-methyl-histidine; X is selected from the group consisting of Ala, Gly, Val, Thr, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and R$_2$ is selected from the group consisting of NH$_2$, and Gly-OH; providing that when R$_1$ is His, X is Ala, Y is Glu, and Z is Glu, R$_2$ must be NH$_2$.

Yet another preferred group of GLP-1 compounds consistent with the present invention is disclosed in WO 91/11457 (U.S. Pat. No. 5,545,618, herein incorporated by reference) and consists essentially of GLP-1(7-34), GLP1(7-35), GLP-1(7-36), or GLP-1(7-37), or the amide forms thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Still other GLP-1 molecules consistent with the present invention have also been described in WO 98/08871, and include a lipophilic substituent attached to the N-terminal or to the C-terminal amino acid residue wherein the substituent is an alkyl group or a group which has an omega carboxylic group.

Because the enzyme, dipeptidyl-peptidase IV (DPP IV), may be responsible for the observed rapid in vivo inactivation of administered GLP-1, [see, e.g., Mentlein, R., et al., *Eur. J. Biochem.*, 214:829–835 (1993)], administration of GLP-1 analogs and derivatives that are protected from the activity of DPP IV is preferred, and the administration of Gly$^8$-GLP-1(7-36)NH$_2$, Val$^8$-GLP-1(7-37)OH, α-methyl-Ala$^8$-GLP-1(7-36)NH$_2$, and Gly$^8$-Gln$^{21}$-GLP-1(7-37)OH, or pharmaceutically-acceptable salts thereof, is more preferred.

The use in the present invention of a molecule claimed in U.S. Pat. No. 5,118,666, herein incorporated by reference, is preferred. Such molecule is selected from the group consisting of a peptide having the amino acid sequence:

His-Ala-Glu-Gly-Thr-Phe-Thr-Ser-Asp-Val-Ser-Ser-Tyr-Leu-Glu-
Gly-Gln-Ala-Ala-Lys-Glu-Phe-Ile-Ala-Trp-
Leu-Val-X      SEQ ID NO:2 wherein X is selected from the group consisting of Lys and Lys-Gly; and a derivative of said peptide, wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

Another preferred group of GLP-1 molecules for use in the present invention consists of compounds disclosed in U.S. Pat. No. 5,512,549, herein incorporated by reference, having the general formula 1:

SEQ ID NO:3

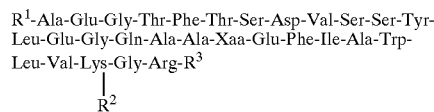

and pharmaceutically-acceptable salts thereof, wherein R$^1$ is selected from the group consisting of 4-imidazopropionyl, 4-imidazoacetyl, or 4-imidazo-a, a dimethyl-acetyl; R$^2$ is selected from the group consisting of C$_6$–C$_{10}$ unbranched acyl, or is absent; R$^3$ is selected from the group consisting of Gly-OH or NH$_2$; and, Xaa is Lys or Arg, may be used in present invention.

More preferred compounds of formula 1 for use in the present invention are those in which Xaa is Arg and R$^2$ is C$_6$–C$_{10}$ unbranched acyl.

Highly preferred compounds of formula 1 for use in the present invention are those in which Xaa is Arg, R$^2$ is C$_6$–C$_{10}$ unbranched acyl, and R$^3$ is Gly-OH.

More highly preferred compounds of formula 1 for use in the present invention are those in which Xaa is Arg, R$^2$ is C$_6$–C$_{10}$ unbranched acyl, R$^3$ is Gly-OH, and R$^1$ is 4-imidazopropionyl.

The most preferred compound of formula 1 for use in the present invention is that in which Xaa is Arg, R$^2$ is C$_8$ unbranched acyl, R$^3$ is Gly-OH, and R$^1$ is 4-imidazopropionyl.

The use of Val$^8$-GLP-1(7-37)OH or a pharmaceutically-acceptable salt thereof, as claimed in U.S. Pat. No. 5,705,483, herein incorporated by reference, in the present invention is highly preferred.

Methods for preparing the GLP-1, GLP-1 analogs, or GLP-1 derivatives useful in the present invention are well-known in the art and are easily within the grasp of ordinarily skilled protein chemists or biochemists. The amino acid portion of the active compound used in the present invention, or a precursor thereto, can be made either by solid-phase synthetic chemistry, purification of GLP-1 molecules from natural sources, or recombinant DNA technology. Routine synthetic organic techniques enable the alkylation and acylation of the GLP-1 derivatives.

The term "GLP-1 related compound" refers to any compound falling within the GLP-1, GLP-1 analog, or GLP-1 derivative definition.

The unexpected effect of nicotinamide on formulation stability was demonstrated by preparing formulations of the present invention, and comparing their turbidity with the turbidity of controls lacking nicotinamide.

Parenteral formulations of the present invention can be prepared using conventional dissolution and mixing procedures. One ordinarily skilled in the formulation sciences will recognize that the order of addition of a medically useful peptide or protein, hydrophobic preservative, and nicotinamide could be varied without compromising the stability of the resulting formulations.

In one embodiment of the invention, nicotinamide may be added to a purified peptide or protein solution and then lyophilized without adversely affecting chemical or physical stability while in the solid state. Upon reconstitution with a diluent which contains a hydrophobic preservative and not containing nicotinamide, the protein formulation exhibits superior physical stability attributable to the presence of nicotinamide in the formulation. Conversely, a stable formulation of the present invention may be prepared by dissolving a measured mass of pure lyophilized protein in water, and then adding measured volumes of nicotinamide and hydrophobic preservative solutions in quantities sufficient to provide the desired concentrations. Optional compounds may also be added, such as an isotonicity agent or a pharmaceutically-acceptable buffer. The pH of the formulation may be adjusted using, for example, hydrochloric acid or sodium hydroxide solutions. Once prepared, the formulations of the present invention are generally sterile-filtered prior to administration. Formulations of the present invention may be prepared by many other processes which are readily apparent to one of ordinary skill in the art. For example, the manner and conditions under which the components are combined, the type of acid or base used to adjust pH, and the method for sterilizing the formulations may be optimized by one of ordinary skill.

The hydrophobic preservative and nicotinamide used in the formulations of the present invention are readily available from commercial suppliers in sufficient quality to meet regulatory requirements for administration to humans.

The formulations of the present invention optionally may contain other compounds in addition to the medically useful peptide or protein, hydrophobic preservative, and nicotinamide. For example, pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) may optionally be added to the formulation to reduce aggregation. These additives are particularly useful if a pump or plastic container is used to administer the formulation. A pharmaceutically acceptable surfactant may further reduce protein aggregation. An isotonicity agent, preferably glycerin, may be optionally added to the soluble, parenteral formulation. The concentration of the isotonicity agent is in the range known in the art for parenteral formulations, preferably about 1 to 25 mg/mL, more preferably about 8 to 16 mg/mL or about 16 mg/mL to about 25 mg/mL., and still more preferably about 16 mg/mL. A pharmaceutically acceptable buffer may optionally be added to control pH.

As noted above, the invention provides soluble formulations comprising a medically useful peptide or protein, a hydrophobic preservative, and nicotinamide. Preferably the nicotinamide concentration is between 0.01 and 2 molar. Other preferred ranges of nicotinamide concentration are: between 0.05 molar and 1.5 molar; between 35 0.1 molar and 1.0 molar; between 0.1 molar and 0.5 molar; between 0.5 molar and 1.0 molar; and between 0.15 molar and 0.25 molar. With nicotinamide added to the formulation, the peptides and proteins remain in solution in the presence of certain preservatives, making possible a multi-use parenteral formulation that is relatively free of protein aggregation.

The phenolic preservatives, used singly or in combination, are preferred preservatives for use in the formulations of the present invention. Another group of preferred preservatives are the alkylparaben preservatives. Benzyl alcohol and benzoic acid are other preferred preseratives. More highly preferred preservatives are phenol and m-cresol, used singly or in combination. When used in combination, the molar ratio of phenol to m-cresol in the formulations is preferably between 3-to-1 and 1-to-3, whereas, the total concentration of preservative is preferably between about 1 mg/mL and 10 mg/mL. The concentration of preservative is that required to maintain preservative effectiveness, which, in turn, may depend on the preservative, its solubility, and the temperature and the pH of the formulation, among other variables. Generally, the amount of preservative necessary can be found in See, e.g., WALLHAUSER, K.-H., DEVELOP. BIOL. STANDARD. 24, pp. 9–28 (Basel, S. Krager, 1974).

In general, the concentration of the medically useful peptide or protein can range from about 0.01 to about 100 mg/mL depending on the pharmacology of the given protein or peptide. For example, the concentration of human growth hormone is from about 0.25 mg/mL to about 40 mg/mL. Preferably, the concentration is from about 0.25 mg/mL to about 25 mg/mL. More preferably, the concentration is from about 0.5 mg/mL to about 10 mg/mL. Other preferred ranges of concentration are from about 0.5 mg/mL to about 15 mg/mL.

The concentrations of GLP-1 related molecules ranges from about 0.01 mg/mL to 10 mg/mL, preferably from about 0.1 mg/mL to about 5 mg/mL, more preferably from about 0.25 mg/mL to about 1 mg/mL. Most preferably, the concentration is from about 0.5 mg/mL to about 1.0 mg/mL.

The solubility of the medically useful peptide or protein in the present formulations is such that the turbidity of the formulation is lower than 50 NTU. More preferably, the turbidity is lower than 20 NTU. Most preferably, the turbidity is lower than 10 NTU.

Peripheral, parenteral administration is preferred. The formulations prepared in accordance with the present invention may be administered using a syringe, injector, pump, or any other device recognized in the art for parenteral administration. The amount of a formulation of the present invention that would be administered to treat a given disease will depend on a number of factors, among which are included, without limitation, the patient's sex, weight and age, the underlying causes of the disease, the route of administration and bioavailability, and the potency of the given peptide or protein. Where administration is intermittent, the amount per administration should also take into account the interval between doses, and the bioavailability of the protein from the formulation. Administration of the formulation of the present invention could be continuous. It is within the skill of the ordinary physician to titrate the dose and rate or frequency of administration of the formulation of the present invention to achieve the desired clinical result.

The present invention may be better understood with reference to the following examples. These examples are intended to be representative of specific embodiments of the invention, and are not intended as limiting the scope of the invention.

EXAMPLE 1

The, following stock solutions were prepared and used to make the tested formulations.

$V^8$-GLP-1(7-37)OH, as described in U.S. Pat. No. 5,705,483, was biosynthesized in recombinant *E. coli*, purified to near homogeneity, and then lyophilized. A sample of the lyophilized peptide was dissolved in water that had been previously adjusted to pH 9.0 with 5 N NaOH to a final concentration of 2 mg/mL. This stock solution was then adjusted to pH 7.8 using 10% HCl.

1 M nicotinamide in water.

100 mM sodium phosphate in water, pH 7.8.

2% phenol (w/v) in water.

1.2% m-cresol (w/v) in water.

Pure benzyl alcohol.

Sterile water for irrigation.

All formulations shown below were prepared at a final concentration of 5 mM phosphate buffer and 0.5 mg/mL $V^8$-GLP-1(7-37)OH. The phosphate buffer, nicotinamide, and $V^8$-GLP-1(7-37)OH stock solutions were filtered through a 0.22 μm filter prior to use. The stock solutions and reagents were mixed in appropriate ratios to obtain the formulations shown below. The order of addition was preservative, nicotinamide, buffer, sterile water, $V^8$-GLP-1. The final pH of the formulations was checked and adjusted to 7.8 if necessary. The clarity of the samples was measured using an HACH 2100AN turbidimeter.

| # | Nicotimamide | Preservative | Initial NTU | NTU after 3 days @ 5° C. |
|---|---|---|---|---|
| 1 | 0 mM | 0.3% m-cresol | 48.495 | 98.14 |
| 2 | 100 mM | 0.3% m-cresol | 3.6365 | 48.89 |
| 3 | 200 mM | 0.3% m-cresol | 0.099 | 32.65 |
| 4 | 300 mM | 0.3% m-cresol | 0.015 | 3.83 |
| 5 | 400 mM | 0.3% m-cresol | 0.0995 | 0.05 |
| 6 | 0 mM | 0.5% phenol | 0.1765 | 44.19 |
| 7 | 100 mM | 0.5% phenol | 0.5965 | 32.48 |
| 8 | 200 mM | 0.5% phenol | 0.2115 | 20.19 |
| 9 | 300 mM | 0.5% phenol | 0.044 | 0.47 |
| 10 | 400 mM | 0.5% phenol | 0.215 | 0.47 |
| 11 | 0 mM | 1.5% benzyl alcohol | −0.1415 | 35.12 |

-continued

| # | Nicotimamide | Preservative | Initial NTU | NTU after 3 days @ 5° C. |
|---|---|---|---|---|
| 12 | 100 mM | 1.5% benzyl alcohol | −0.055 | 22.89 |
| 13 | 200 mM | 1.5% benzyl alcohol | −0.0165 | −0.5 |
| 14 | 300 mM | 1.5% benzyl alcohol | 0.1465 | 0.42 |
| 15 | 400 mM | 1.5% benzyl alcohol | 0.078 | 0.28 |

EXAMPLE 2

A stock solution containing 5 mg/mL of GLP-1(737)OH in 70 mM phosphate buffer at pH 7.4 was prepared and sterile filtered through a 0.22 μm filter. A stock of 1% m-cresol was prepared in water and sterile filtered through a 0.22 μm filter. A stock solution of 2 M nicotinamide was prepared in water and sterile filtered through a 0.22 μm filter. The stocks were mixed as indicated:

| GLP stock | m-cresol stock | Nicotinamide stock | DI water | Final conc. nicotinamide |
|---|---|---|---|---|
| 0.800 ml | 1.200 ml | 0 ml | 2.000 ml | 0 mM |
| 0.800 ml | 1.200 ml | 0.500 ml | 1.500 ml | 250 mM |
| 0.800 ml | 1.200 ml | 1.000 ml | 1.000 ml | 500 mM |
| 0.800 ml | 1.200 ml | 1.500 ml | 0.500 ml | 750 mM |
| 0.800 ml | 1.200 ml | 2.000 ml | 0 ml | 1000 mM |

All final formulations were prepared at a 4.0 ml volume and contained 1 mg/ml GLP-1(7-37)OH, 14 mM phosphate buffer at pH 7.4 with 0.3% m-cresol as a preservative. Please note: the nicotinamide and protein were always mixed prior to the addition of preservative. The GLP formulations were aged at 25° C. All nicotinamide containing formulations demonstrated good physical stability over 4 days measuring less than 10 NTU. All non-nicotinamide formulations measured greater than 65 NTU.

EXAMPLE 3

A stock containing 20 mg/ml of hGH in 20 mM citrate buffer at pH 7.5 was prepared and sterile filtered through a 0.22 μm filter. A stock of 1.5% m-cresol was prepared in water and sterile filtered through a 0.22 μm filter. The stocks were mixed as indicated:

| hGH stock | m-cresol stock | Nicotinamide added | Final conc. nicotinamide |
|---|---|---|---|
| 5.0 ml | 2.0 ml | 0 mg | 0 mM |
| 5.0 ml | 2.0 ml | 611 mg | 500 mM |
| 5.0 ml | 2.0 ml | 916 mg | 750 mM |
| 5.0 ml | 2.0 ml | 1221 mg | 1000 mM |

All final formulations were prepared at 10 ml volume and contained 10 mg/ml hGH, 10 mM citrate buffer at pH 6.0 with 0.3% m-cresol as a preservative. Please note: the nicotinamide and protein were always mixed prior to the addition of preservative. Results are shown in FIG. 1. The 200 NTU value for the non-nicotinamide formulation represented the limit of detection for the instrument used. The actual value was probably much greater.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

I claim:

1. A soluble formulation comprising a medically useful GLP-1 molecule, a hydrophobic preservative, and nicotinamide.

2. The soluble formulation of claim 1 wherein the GLP-1 molecule is selected from the group consisting of GLP-1 analogs and GLP-1 derivatives.

3. The soluble formulation of claim 1 wherein the GLP-1 molecule is a GLP-1 analog.

4. The soluble formulation of claim 3 wherein the GLP-1 analog is selected from the group consisting of $Val^8$-GLP-1(7-37)OH, $Gly^8$-GLP-1(7-37)OH, and $Asp^8$-GLP-1(7-37)OH.

5. The soluble formulation of claim 4 wherein the GLP-1 analog is $Val^8$-GLP-1(7-37)OH.

6. The soluble formulation of claim 4 wherein the GLP-1 analog is $Gly^8$-GLP-1(7-37)OH.

7. The soluble formulation of claim 1 wherein the GLP-1 molecule is a GLP-1 derivative.

8. The soluble formulation of claim 7 wherein the GLP-1 derivative is an acylated GLP-1 derivative.

9. The soluble formulation of claim 8 wherein the GLP-1 molecule is a GLP-1 derivative prepared by the process of acylating a GLP-1 analog selected from the group consisting of GLP-1(7-34), GLP-1(7-35), GLP-1(7-36), GLP-1(7-37), and the amide forms thereof, with at least one modification selected from the group consisting of:

(a) substitution of a glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of a glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution according to at least one of:
Y for V at position 16;
K for S at position 18;
D for E at position 21;
S for G at position 22;
R for Q at position 23;
R for A at position 24; and
Q for K at position 26;

(d) substitution comprising at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine or the D or N-acylated or alkylated form of histidine for histidine at position 7.

10. The soluble formulation of claim 9 wherein the GLP-1 analog has an arginine substituted for lysine at position 34.

11. The soluble formulation of claim 10 wherein the GLP-1 analog is acylated on the epsilon-amino group of lysine.

12. The soluble formulation of claim 1, wherein the concentration of the medically useful GLP-1 molecule is between 0.01 mg/mL and 100 mg/mL.

13. The soluble formulation of claim 1, wherein the preservative is selected from the group consisting of phenol, cresol, alkylparaben, benzyl alcohol, benzoic acid, chlorobutanol and mixtures thereof.

14. The soluble formulation of claim 1, wherein the preservative is phenol, m-cresol, methylparaben, propylparaben, chlorocresol, benzyl alcohol, or mixtures thereof.

15. The soluble formulation of claim 1, wherein the nicotinamide concentration is greater than 0.01 molar and less than 2.0 molar.

16. The soluble formulation of claim 1, wherein the nicotinamide concentration is greater than 0.1 molar and less than 1.0 molar.

17. The soluble formulation of claim 1, which further comprises an isotonicity agent.

18. The soluble formulation of claim 1, which further comprises a pharmaceutically acceptable buffer.

19. A process for preparing a soluble formulation of claim 1, which comprises combining the medically useful GLP-1 molecule, a hydrophobic preservative, and nicotinamide.

20. A method of treating diabetes in a mammal in need thereof, which comprises administering to said mammal the soluble formulation of claim 1.

21. An article of manufacture, comprising packaging material and a vial comprising a solution of a formulation of claim 1, wherein said packaging material comprises a label which indicates that such solution may be used to treat disease.

* * * * *